United States Patent [19]

Lincoln

[11] 4,172,206
[45] Oct. 23, 1979

[54] PHENACYL ESTER OF PGF$_2\alpha$

[75] Inventor: Frank H. Lincoln, Portage, Mich.

[73] Assignee: The Upjohn Company, Kalamazoo, Mich.

[21] Appl. No.: 900,355

[22] Filed: Apr. 26, 1978

Related U.S. Application Data

[62] Division of Ser. No. 497,243, Aug. 14, 1974.

[51] Int. Cl.$^2$ .......................................... C07C 177/00
[52] U.S. Cl. .................................... 560/121; 424/305
[58] Field of Search ......................................... 560/121

[56] References Cited

U.S. PATENT DOCUMENTS 3,984,454  10/1976  Skuballa et al. ................. 260/468

OTHER PUBLICATIONS

Shriner et al., Organic Compounds, p. 200 (1963).

Primary Examiner—Robert Gerstl
Attorney, Agent, or Firm—Morris L. Nielsen

[57]  ABSTRACT

The phenacyl ester of PGF$_2\alpha$ represented by the formula

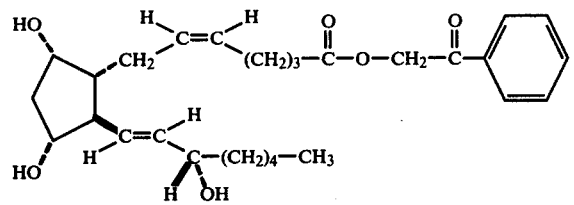

is disclosed. The compound is useful for the same pharmacological and medical purposes as PGF$_2\alpha$, is useful in crystalline form as a convenient form for ease of handling, administering, and purifying.

2 Claims, No Drawings

PHENACYL ESTER OF PGF$_{2\alpha}$

This is a division of application Ser. No. 497,243 Pending, filed Aug. 14, 1974.

BACKGROUND OF THE INVENTION

This invention relates to novel ester derivatives of prostaglandin F$_{2\alpha}$ (hereinafter identified as "PGF$_{2\alpha}$"), 15(S)-15-methyl-PGF$_{2\alpha}$, and 15(R)-15-methyl-PGF$_{2\alpha}$, including their racemic compounds, and to processes for producing them.

PGF$_{2\alpha}$ is represented by the formula:

[Structure I]

A systematic name for PGF$_{2\alpha}$ is 7-{3α,5α-dihydroxy-2β-[(3S)-3-hydroxy-trans-1-octenyl]-1α-cyclopentyl}-cis-5-heptenoic acid. PGF$_{2\alpha}$ is known to be useful for a variety of pharmacological and medical purposes, for example, labor induction and abortion in pregnant animals, including humans, menstrual regulation in both pregnant and non-pregnant animals, including humans, treatment of asthma, and the inhibition of blood platelet aggregation. See Bergstrom et al., Pharmacol. Rev. 20, 1 (1968) and references cited therein. As to racemic PGF$_{2\alpha}$, see for example W. P. Schneider, Chem. Commun. 304 (1969).

The 15-methyl-PGF$_{2\alpha}$ analogs are represented by the formula:

[Structure II]

wherein M' is

[CH$_3$ OH or CH$_3$ OH]

following the usual convention wherein broken line attachment of hydroxy to the side chain at carbon 15 indicates the natural or "S" configuration. See for example Nugteren et al., Nature 212, 38 (1966) and Cahn, J. Chem. Ed. 41, 116 (1964). The 15-methyl-PGF$_{2\alpha}$ analogs in their optically active and racemic forms are known. See for example U.S. Pat. Nos. 3,728,382 and 3,804,890.

Esters of the above compounds are known, wherein the hydrogen atom of the carboxyl group is replaced by a hydrocarbyl or substituted hydrocarbyl group. Among these are the methyl ester of PGF$_{2\alpha}$ (B. Samuelsson, J. Biol. Chem. 238, 3229 (1963)), the phenyl and alkyl-phenyl esters of PGF$_{2\alpha}$ (British Spec. 1,282,661, Derwent Farmdoc No. 67438R), the α-naphthyl ester of PGF$_{2\alpha}$ (Belgian Patent No. 775,106, Derwent Farmdoc No. 33705T) and the methyl esters of 15(S)-15-methyl-PGF$_{2\alpha}$ and of 15(R)-methyl-PGF$_{2\alpha}$ (U.S. Patents cited above).

SUMMARY OF THE INVENTION

It is a purpose of this invention to provide novel ester derivatives of PGF$_{2\alpha}$, 15(S)-15-methyl-PGF$_{2\alpha}$, and 15(R)-15-methyl-PGF$_{2\alpha}$ and their racemic compounds. It is a further purpose to provide such esters in a free-flowing crystalline form. It is still a further purpose to provide novel processes for preparing these esters.

The presently described phenacyl-type esters include compounds represented by the generic formula:

[Structure III]

wherein M is

[H OH, CH$_3$ OH, or CH$_3$ OH];

wherein R$_1$ is phenyl, p-bromophenyl, p-biphenylyl, p-nitrophenyl, p-benzamidophenyl, or 2-naphthyl; and wherein R$_2$ is hydrogen or benzoyl. Accordingly, in the presently described esters, the group $$-\underset{\underset{R_2}{|}}{CH}-\overset{O}{\underset{\|}{C}}-R_1$$

is exemplified by:

A  —CH$_2$—C(=O)—C$_6$H$_5$

B  —CH$_2$—C(=O)—C$_6$H$_4$—Br

C  —CH$_2$—C(=O)—C$_6$H$_4$—C$_6$H$_5$

D  —CH$_2$—C(=O)—C$_6$H$_4$—NO$_2$

E  —CH$_2$—C(=O)—C$_6$H$_4$—NH—C(=O)—C$_6$H$_5$

F  —CH$_2$—C(=O)—(2-naphthyl)

-continued

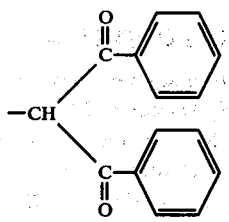
G

For example, PGF$_{2\alpha}$, phenacyl ester, is represented by formula III when M is

and wherein

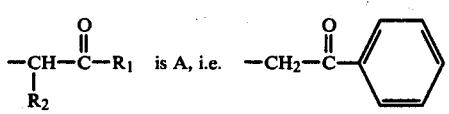  is A, i.e.

and is conveniently identified herein as the PGF$_{2\alpha}$ ester of formula III-A. Racemic compounds are designated by the prefix "racemic" or "dl"; when that prefix is absent, the intent is to designate an optically active compound. For example, racemic 15-methyl-PGF$_{2\alpha}$, p-benzamidophenacyl ester, corresponds to formula III wherein M is

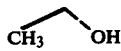

and wherein

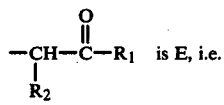  is E, i.e.

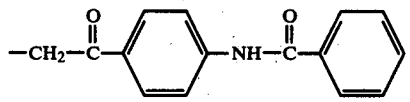

including of course not only the optically active isomer represented by formula III but also its enantiomer.

The novel formula -III compounds and corresponding racemic compounds of this invention are each useful for the same purposes as described above for PGF$_{2\alpha}$ and are used for those purposes in the same manner known in the art, including oral, sublingual, buccai, rectal, intravaginal, intrauterine, or topical administration.

For many applications these novel prostaglandin esters which we have obtained from certain specified phenacyl-type halides have advantages over the corresponding known prostaglandin compounds. Thus, these phenacyl-type esters are surprisingly stable compounds having outstanding shelf-life and thermal stability. In oral administration these esters have shown surprisingly greater efficacy than the corresponding free acids or lower alkyl esters, whether because of longer duration of biological activity or because of improved lipophilicity and absorption is not certain. These esters offer a further advantage in that they have low solubility in water and the body fluids and are therefore retained longer at the site of administration.

A particularly outstanding advantage of many of these phenacyl-type esters is that they are obtained in free-flowing crystalline form, generally of moderately high melting point, in the range 50°–130° C. This form is especially desirable for ease of handling, administering, and purifying. These crystals are highly stable, for example showing practically no decomposition at accelerated storage tests, in comparison with liquid alkyl esters or the free acids. This quality is advantageous because the compound does not lose its potency and does not become contaminated with decomposition products.

These crystalline esters also provide a means of purifying PGF$_{2\alpha}$ and 15(S)-15-methyl-PGF$_{2\alpha}$, which are first converted to one of these esters, crystallized and recrystallized until pure, and then recovered as the free acid. One method of recovering the free acid is by enzymatic hydrolysis of the ester, for example with a lipase. See German Patent No. 2,242,792, Derwent Farmdoc No. 23047U.

A p-iodophenacyl ester of 15(S)-15-methyl-PGF$_{2\alpha}$ was useful for X-ray crystallographic structure determination, E. W. Yankee et al., J. Am. Chem. Soc. 94, 3651 (1972). Various phenacyl esters have been useful for characterizing aliphatic acids because of their sharp melting points, Shriner and Fuson, "Systematic Identification of Organic Compounds", 3rd Ed., pp. 154–157 (1948).

Especially preferred of the novel compounds of this invention are those compounds which are in free-flowing crystalline form, for example:

phenacyl ester of PGF$_{2\alpha}$
p-phenylphenacyl ester of PGF$_{2\alpha}$
p-nitrophenacyl ester of PGF$_{2\alpha}$
p-benzami dophenacyl ester of PGF$_{2\alpha}$
p-naphthoylmethyl ester of PGF$_{2\alpha}$
α-benzoylphenacyl ester of PGF$_{2\alpha}$ and
p-bromophenacyl ester of 15(S)-15-methyl-PGF$_{2\alpha}$.

The phenacyl-type esters of PGF$_{2\alpha}$, 15(S)-15-methyl-PGF$_{2\alpha}$, and 15(R)-15-methyl-PGF$_{2\alpha}$ and their racemic compounds encompassed by formula III wherein

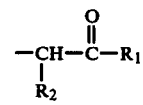

is defined by ester groups A through G are produced by the reactions and procedures described and exemplified hereinafter. For convenience, the prostaglandin or prostaglandin analog is referred to as "the PG compound". The term "phenacyl" is used in a generic sense, including also substituted phenyl and naphthyl derivatives.

Various methods are available for preparing these esters. Thus, by one method, the PG compound is converted to a sodium salt by methods known in the art and reacted with an appropriate phenacyl halide in a solvent.

Preferred, however, is the method of simply mixing the PG compound with a phenacyl halide, preferably the bromide, and a tertiary amine in a solvent and letting the reaction proceed at a temperature generally between 20° and 70° C. The course of the reaction is readily followed by sampling the mixture and subjecting the samples to thin layer chromatography, usually being complete within 0.25–4.0 hr. Thereafter the reaction mixture is worked up to yield the ester following methods described herein or known in the art, for example the product being purified by silica gel chromatography.

Examples of the phenacyl-type halides useful for this purpose are: phenacyl bromide, p-bromophenacyl bromide, p-phenylphenacyl bromide, p-nitrophenacyl bromide, p-benzamidophenacyl bromide, 2-bromo-2′-acetonaphthone, and 2-bromo-1,3-diphenyl-1,3-propanedione. In using these reagents the usual precautions are taken to avoid their lachrymatory effects.

Examples of suitable tertiary amines are triethylamine, diethylmethylamine, diisopropylethylamine, dimethylisobutylamine, and dimethylaniline.

Examples of suitable solvents are acetonitrile, dioxane, tetrahydrofuran and N,N-dimethylformamide.

The phenacyl halide is preferably used in equivalent amounts or in excess to insure that all of the PG compound is converted to ester. Excess phenacyl halide is separated from the product by methods described herein or known in the art, for example by chromatography. The tertiary amine is mainly used as a basic catalyst for the esterification but can also be used in larger amounts as the solvent.

Solid esters are converted to a free-flowing crystalline form on crystallization from a variety of solvents, including ethyl acetate, tetrahydrofuran, methanol, ethanol, and acetone, by cooling or evaporating a saturated solution of the ester in the solvent or by adding a miscible nonsolvent such as diethyl ether, hexane, or water. The crystals are then collected by conventional techniques, e.g. filtration or centrifugation, washed with a small amount of solvent, and dried under reduced pressure. They may be dried in a current of warm nitrogen or argon, or by warming at about 60°–75° C., taking care not to exceed the melting point. Although the crystals are normally pure enough for many applications, they may be crystallized by the same general techniques to achieve improved purity after each recrystallization.

DESCRIPTION OF THE PREFERRED EMBODIMENTS

The invention can be more fully understood by the following examples.

All temperatures are in degrees centigrade.

Silica gel chromatography, as used herein, is understood to include chromatography on a column packed with silica gel, elution, collection of fractions, and combination of those fractions shown by thin layer chromatography (TLC) to contain the desired product free of starting material and impurities.

"TLC", herein, refers to thin layer chromatography.

EXAMPLE 1

PGF$_{2\alpha}$, Phenacyl Ester (Formula III-A wherein M is

).

A mixture of PGF$_{2\alpha}$ (0.20 g.), phenacyl bromide (0.25 g.), and 6 ml. of 0.5% aqueous sodium carbonate in 15 ml. of methanol is heated under reflux with stirring for 1.5 hr. The mixture is partially concentrated under reduced pressure and the residue is extracted with dichloromethane. The organic phase is washed with dilute aqueous sodium bicarbonate, dried, and concentrated. The resulting residue is subjected to silica gel chromatography, eluting with 40–100% ethyl acetate in Skellysolve B. The residue obtained by concentration of selected fractions is crystallized from diethyl ether as the title compound, white free-flowing crystals, 0.151 g., m.p. 66°–67° C. (recrystd.), having infrared absorption bands at 3200, 1740, 1695, 1225, 1155, 1135, 1060, 1020, 965, 760, 690 cm$^{-1}$.

Following the procedure of Example 1 but employing p-bromophenacyl bromide instead of phenacyl bromide, there is obtained the corresponding p-bromophenacyl ester of PGF$_{2\alpha}$.

EXAMPLE 2

PGF$_{2\alpha}$, p-Phenylphenacyl Ester (Formula III-C wherein M is

).

A mixture of PGF$_{2\alpha}$ (1.92 g.), p-phenylphenacyl bromide (2.29 g.), and 0.97 ml. of triethylamine in 50 ml. of acetonitrile is heated at 60° C. until TLC shows conversion to the ester, about 45 min. The reaction mixture is partitioned between 100 ml. ethyl acetate and 200 ml. of 0.2 N. aqueous citrate, pH 3.0. The organic phase is washed with 100 ml. of water, dried, and concentrated under reduced pressure. The residue is subjected to silica gel chromatography, eluting with chloroform-acetone (1:4). The residue obtained by concentration of selected fractions is crystallized from ethyl acetate-hexane as the title compound, white free-flowing cyrstals, 0.248 g., m.p. 105.3°–110° C., having R$_f$ 0.3 (TLC on silica gel in ethyl acetate).

EXAMPLE 3

PGF$_{2\alpha}$, p-Nitrophenacyl Ester (Formula III-D wherein M is

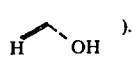).

Following the procedure of Example 2 but using 4.168 g. of PGF$_{2\alpha}$, 3.432 g. of p-nitrophenacyl bromide, and 1.87 ml. of triethylamine, heated in tetrahydrofuran at 60° for 15 min., there is obtained a crude residue. This residue is subjected to silica gel chromatography, eluting with 300 ml. chloroform-ethyl acetate (1:1) followed by ethyl acetate. The residue obtained by concentration of selected fractions is crystallized from ethyl acetate, upon addition of hexane as the title compound, free-flowing crystals, 4.49 g., m.p. 84.8°–86.0° C., having R$_f$ 0.4 (TLC on silica gel in ethyl-acetate-acetic acid (97.3)).

EXAMPLE 4

PGF$_{2\alpha}$, p-Benzamidophenacyl Ester (Formula III-E wherein M is

Following the procedure of Example 2 but using 0.350 g. of PGF$_{2\alpha}$, 0.720 g. of p-benzamidophenacyl bromide, and 2.0 ml. of diisopropylethylamine in 25 ml. acetonitrile at 35° for 30 min. there is obtained a crude residue. This residue is subjected to silica gel chromatography, eluting with 400 ml. ethyl acetate-hexane (7:3) followed with 100 ml. ethyl acetate and finally 450 ml. tetrahydrofuran. The residue obtained by concentration of selected fractions is crystallized from ethylacetate upon addition of hexane, as the title compound, 328 mg., m.p. 132.3°–135.0° having R$_f$0.3 (TLC on silica gel in ethyl acetate-acetic acid, 97:3).

EXAMPLE 5

PGF$_{2\alpha}$, 2-Naphthoylmethyl Ester (Formula III-F wherein M is

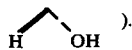).

Following the procedure of Example 2 using 0.515 g. of PGF$_{2\alpha}$, 0.424 g. of 2-bromo-2'-acetonaphthone, and 0.277 ml. of diisopropylethylamine in 10 ml. of acetonitrile, and crystallizing from ethyl acetate-hexane, there is obtained a crude solid product, 0.542 g. This product is subjected to silica gel chromatography, eluting with ethyl acetate-acetone (4:1). The residue obtained by concentration of selected fractions, an oil, 0.322 g., is crystallized from ethyl acetate-hexane as the title compound, white free-flowing crystals, 0.287 g., m.p. 79.0°–80.0° C., having R$_f$0.6 (TLC on silica gel in ethyl acetate-acetone (4:1)).

EXAMPLE 6

PGF$_{2\alpha}$, α-Benzoylphenacyl Ester (Formula III-G, wherein M is

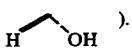).

Following the procedure of Example 2 but using 0.719 g. of PGF$_{2\alpha}$, 0.606 g. of 2-bromo-1,3-diphenyl-1,3-propanedione, and 0.348 ml. of diisopropylethylamine in 10 ml. acetonitrile at 70° C. for 30 min. there is obtained a crude residue. This residue is subjected to silica gel chromatography, eluting with ethyl acetate-acetone-water (70:30:3). The residue obtained by concentration of selected fractions is crystallized from ethyl acetate upon addition of hexane as the title compound, free-flowing crystals 322 mg., m.p. 111.3°–114.0° C., having R$_f$0.6 (TLC on silica gel in ethyl acetate-acetone (1:1)).

EXAMPLE 7

15(S)-15-Methyl-PGF$_{2\alpha}$, p-Bromophenacyl Ester (Formula III-B, wherein M is

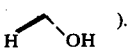).

A mixture of 15(S)-15-methyl-PGF$_{2\alpha}$ (0.114 g.), p-bromophenacyl bromide (0.171 g.), and 3 ml. of aqueous 0.5% sodium carbonate solution in 9 ml. of methanol is stirred at about 25° C. for 90 hr., then reflux for 1.5 hr. The mixture is concentrated under reduced pressure and the residue is taken up in dichloromethane. The organic phase is washed with dilute aqueous sodium bicarbonate, dried and concentrated. The residue is subjected to silica gel chromatography eluting with 5–40% acetone in dichloromethane. The residue obtained by concentration of selected fractions is crystallized from diethyl ether-hexane (1:1) as the title compound, white free-flowing crystals, 0.04 g., m.p. 86.5°–87.5° C.

Following the procedures of Examples 1–7 but employing the racemic forms of the PG compounds, there are obtained the corresponding esters of racemic PG compounds.

EXAMPLES 8–13

The phenacyl-type esters of 15(S)-15-methyl-PGF$_{2\alpha}$ of Table I below are obtained following the procedures of Example 4, wherein the prostaglandin compound is reacted in the presence of diisopropylethylamine with the appropriate phenacyl halide reagent listed in the Table. The crude products, obtained by concentration under reduced pressure, are purified by means described herein or known in the art, including partitioning, solvent extraction, washing, silica gel chromatography, trituration, or crystallization.

Following the procedures of Examples 8–13 but employing the racemic form of the PG compound, there are obtained the corresponding esters of the racemic PG compound.

TABLE I

Esters of 15(S)-15-Methyl PGF$_{2\alpha}$ (Refer to formula III wherein M is 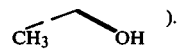 )

| Example | Phenacyl Halide | Product 15(S)-15-Methyl-PGF$_{2\alpha}$ ester of formula: |
|---|---|---|
| 8 | phenacyl bromide | III-A |
| 9 | p-phenylphenacyl bromide | III-C |
| 10 | p-nitrophenacyl bromide | III-D |
| 11 | p-benzamidophenacyl bromide | III-E |
| 12 | 2-bromo-2'-acetonaphthone | III-F |
| 13 | 2-bromo-1,3-diphenyl-1,3-propanedione | III-G |

EXAMPLE 14

15(R)-15-Methyl-PGF$_{2\alpha}$, p-Nitrophenacyl Ester (Formula III-D wherein M is

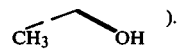).

Following the procedures of Example 4, but using 15(R)-15-methyl-PGF$_{2\alpha}$ (0.182 g.), p-nitrophenacyl bromide (0.350 g.), and diisopropylethylamine (0.11 ml.) in acetonitrile (5 ml.), there is obtained a crude residue. This residue is subjected to silica gel chromatography, eluting with dichloromethane-acetonitrile-methanol (30:70:1) to yield the title compound, 0.19 g., a colorless oil having R$_f$ 0.6 (TLC) on silica gel in dichloromethane-acetonitrile (3:7)).

Likewise following the procedures of Example 4 but using 15(R)-15-methyl-PGF$_{2\alpha}$ with each of the phenacyl halide reagents of Table II, there are obtained the corresponding phenacyl-type esters of 15(R)-15-methyl-PGF$_{2\alpha}$ of Table II.

Likewise following the procedures of Examples 15–20 but employing the racemic forms of the PG compound, there are obtained the corresponding esters of the racemic PG compound.

TABLE II
Esters of 15(R)-15-Methyl-PGF$_{2\alpha}$ (Refer to formula III wherein M is 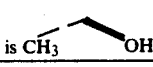).

| Example | Phenacyl Halide | Product 15(R)-15-Methyl-PGF$_{2\alpha}$ ester of formula: |
|---------|-----------------|-----------------------------------------------------------|
| 15 | phenacyl bromide | III-A |
| 16 | p-bromophenacyl bromide | III-B |
| 17 | p-phenylphenacyl bromide | III-C |
| 18 | p-benzamidophenacyl bromide | III-E |
| 19 | 2-bromo-2'-acetonaphthone | III-F |
| 20 | 2-bromo-1,3-diphenyl-1,3-propanedione | III-G |

I claim:

1. The phenacyl ester of PGF$_{2\alpha}$.

2. Free-flowing crystals of a compound of the formula:

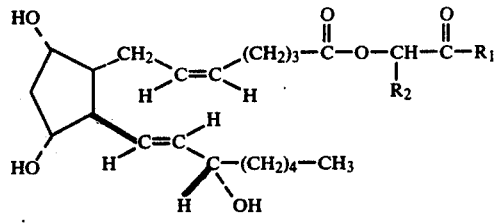

wherein

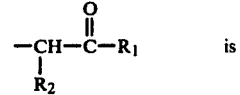 is

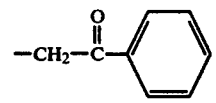

* * * * *